United States Patent [19]
Moss et al.

[11] Patent Number: 5,397,222
[45] Date of Patent: Mar. 14, 1995

[54] REUSABLE MEDICAL CASSETTE FOR AMBULATORY MEDICAL INFUSION PUMPS

[76] Inventors: Richard Moss, 4928 Panorama Cir., West Bloomfield, Mich. 48323; Frederick L. Erlich, 34536 Quaker Valley, Farmington Hills, 48331

[21] Appl. No.: 145,866

[22] Filed: Nov. 1, 1993

[51] Int. Cl.6 ............................................. F04B 43/08
[52] U.S. Cl. ................................ 417/477.2; 604/153
[58] Field of Search ......................... 417/474–477, 417/360; 604/153, 154

[56] References Cited

U.S. PATENT DOCUMENTS

| | | | |
|---|---|---|---|
| D. 232,085 | 7/1979 | Benzing | D16/2 C |
| D. 247,820 | 5/1978 | Stuetzer | D24/15 |
| D. 294,733 | 3/1988 | Peterson et al. | D24/8 |
| D. 326,153 | 5/1992 | Eastman et al. | D24/111 |
| 4,187,057 | 2/1980 | Xanthopoulos | 417/63 |
| 4,236,880 | 12/1980 | Archibald | 417/478 |
| 4,256,437 | 3/1981 | Brown | 417/45 |
| 4,274,407 | 6/1981 | Scarlett | 128/213 R |
| 4,398,908 | 8/1983 | Siposs | 604/31 |
| 4,410,322 | 10/1983 | Archibald | 604/153 |
| 4,468,221 | 8/1984 | Mayfield | 604/152 |
| 4,559,038 | 12/1985 | Berg et al. | 604/153 |
| 4,565,542 | 1/1986 | Berg . | |
| 4,569,674 | 2/1986 | Phillips et al. | 604/119 |
| 4,650,469 | 3/1987 | Berg et al. | 604/131 |
| 4,667,854 | 5/1987 | McDermott et al. | 222/101 |
| 4,673,334 | 6/1987 | Allington et al. | 417/477 A |
| 4,735,558 | 4/1988 | Kienholz et al. | 417/477 A |
| 4,755,109 | 7/1988 | Butts | 417/360 |
| 4,845,487 | 7/1989 | Frantz et al. | 340/679 |
| 4,861,242 | 8/1989 | Finsterwald | 417/477 A |
| 4,978,335 | 12/1990 | Arthur, III | 604/67 |
| 5,213,483 | 5/1993 | Flaherty et al. | 417/477 |
| 5,266,013 | 11/1993 | Aubert et al. | 417/360 |
| 5,299,937 | 10/1993 | Aubert | 417/475 |

*Primary Examiner*—Richard A. Bertsch
*Assistant Examiner*—Peter Korytnyk
*Attorney, Agent, or Firm*—Reising, Ethington, Barnard, Perry & Milton

[57] ABSTRACT

A reusable cassette assembly (14) for an ambulatory medical infusion pump (10) with a reservoir bag (22) has a pump plate 16 removably attached to the shell (18). The pump plate includes a retainer (30) and latch (50) that have distal ends (44) and (56) spaced from the upper surface (26) of the pump plate to allow the tube (22) of the reservoir bag (22) to be laterally engaged or disengaged thereunder. The plate has a slot (25) that is opened or closed by a removable wall section (63) of the shell (18) to allow the tube to laterally disengage from the slot (25).

12 Claims, 4 Drawing Sheets

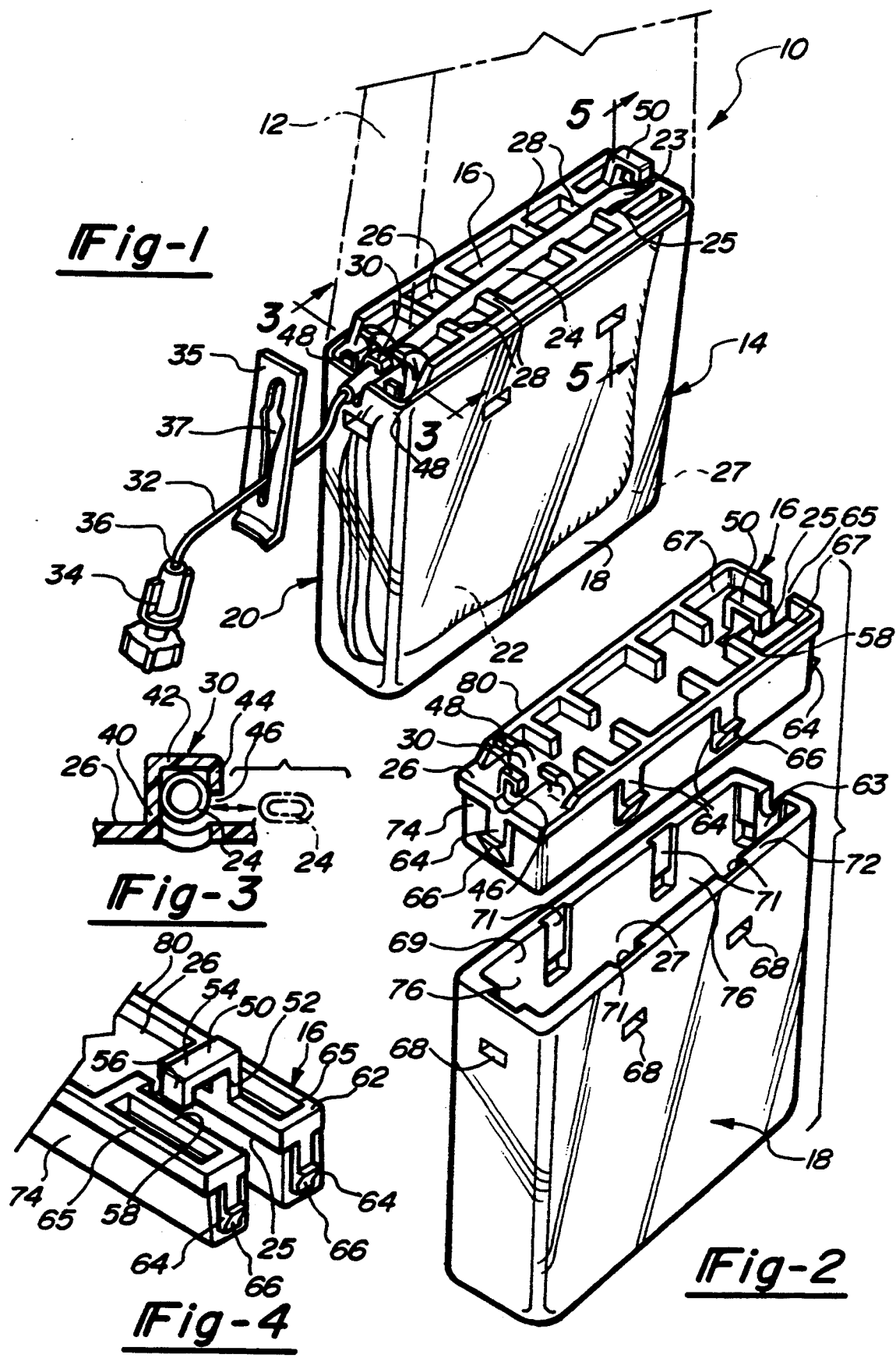

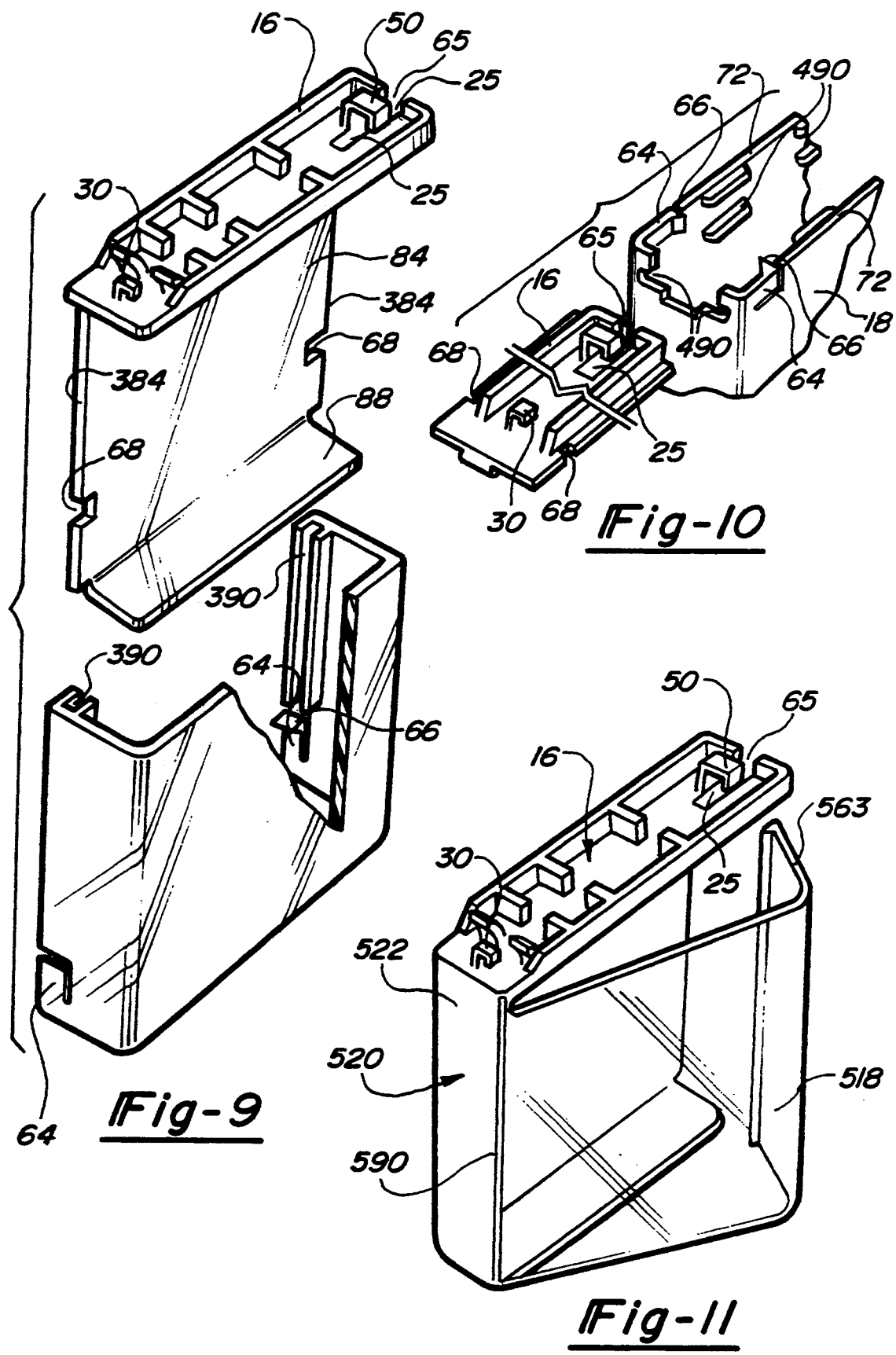

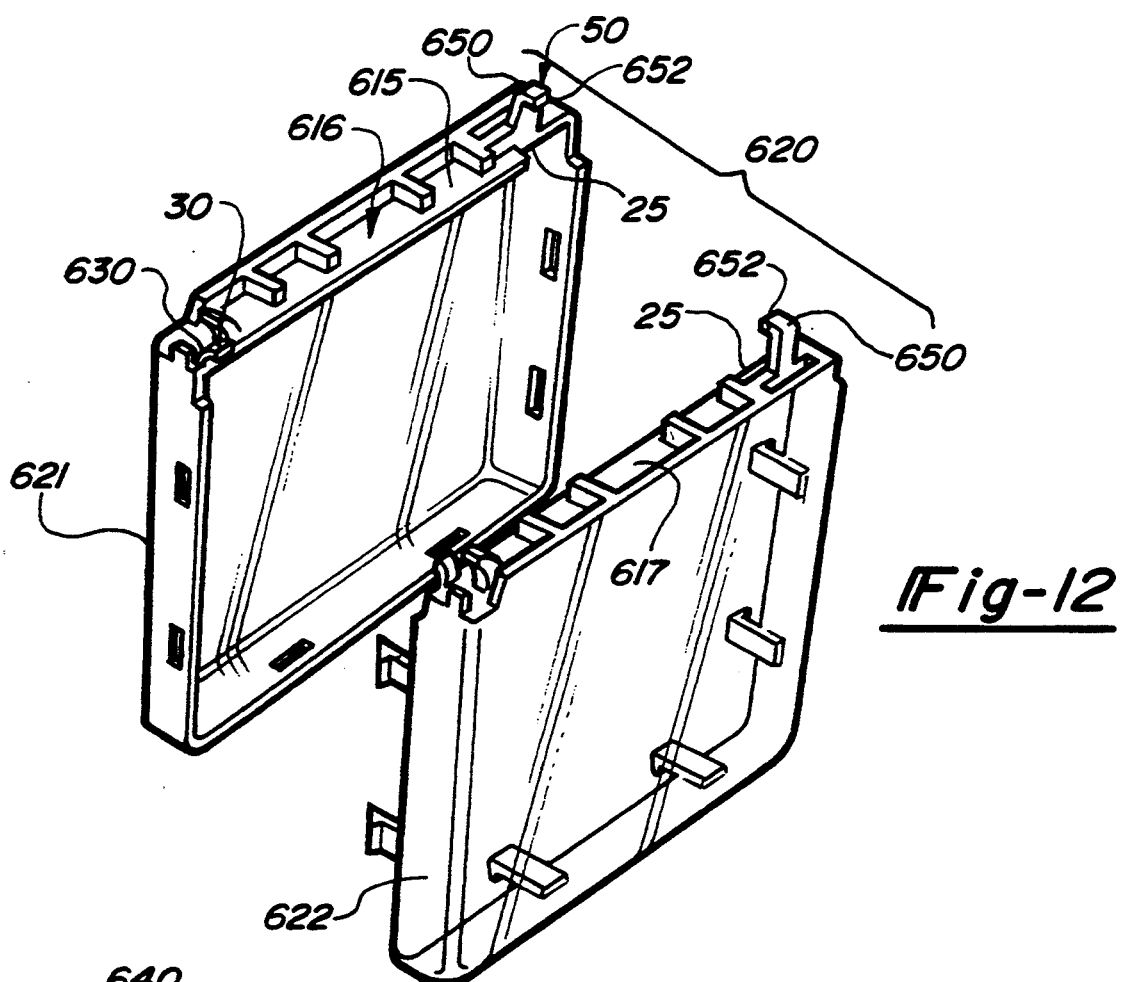
*Fig-12*
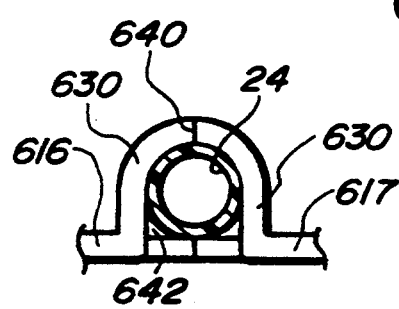
*Fig-13*
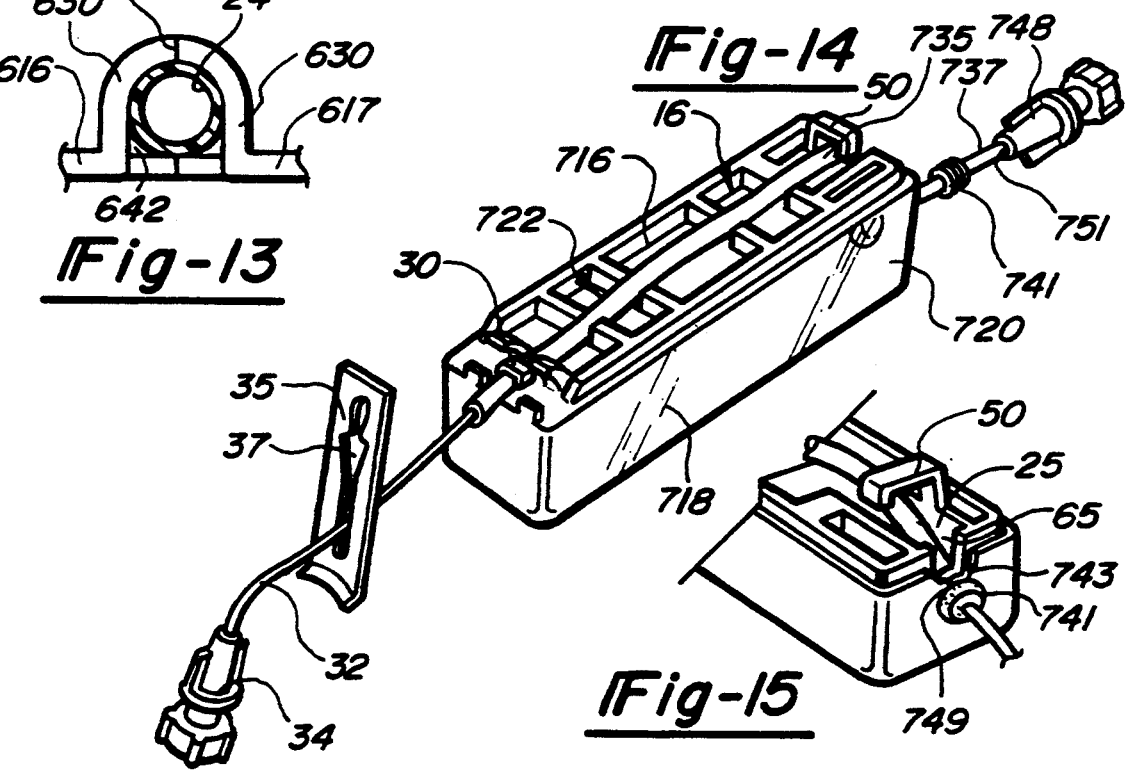
*Fig-14*
*Fig-15*

REUSABLE MEDICAL CASSETTE FOR AMBULATORY MEDICAL INFUSION PUMPS

TECHNICAL FIELD

The field of this invention relates to a reusable pump cassette for an ambulatory medical infusion pump.

BACKGROUND OF THE DISCLOSURE

Ambulatory medical infusion pumps are a commercially successful and popular medical instruments. The pumps allow for the convenient continuous and calibrated delivery of a variety of medicines including but not limited to antibiotics, pain relieving drugs, and chemotherapy drugs.

The pump has a fastener system that allows a supply tube to be removably attached to the pump. The supply tube can be installed on a cassette that has a soft pliable drug reservoir bag placed within a hard shell made from a rigid plastic such as a poly-carbonate to protect the integrity of the bag. The supply tube has a soft section positioned within the pump assembly which is squeezed between the pump and the cassette pump plate to draw or pump the medicine through the supply tube.

The soft tube section is attached to microbore tubing that exits the pump assembly. The microbore tubing has a luer lock or similar connector attached to its distal end that allows connection to a intravenous infusion or subcutaneous delivery system. The microbore tubing resists any unintentional kinking or crimping thus assuring proper delivery of the drugs therethrough.

The pump plate of the pump cassette is permanently secured either by adhesive or sonic welding to the cassette shell to assure that the shell is not unintentionally removed from about the bag so that the bag does not become accidentally exposed and maintains its integrity against accidental puncture.

Often larger amounts of medicine are needed by the patient. Instead of using numerous cassettes with a small bag in each cassette, a larger remote bag of medicine is used. The cassette that attaches to the pump includes only a soft supply tube that engages the pump, a microbore outlet tube that attaches to the patient and a microbore inlet tube that attaches to the remote bag. The inlet tube and outlet tube have distal ends permanently attached to fittings such as luer locks. The fittings maintain the tube assembly permanently secured to the cassette. The microbore tubes are permanently connected to opposing ends of the soft supply tube. The cassette is constructed to permanently retain the supply tube in place. This cassette assembly is often referred to as a remote reservoir cassette or remote cassette.

When the medicine needs to be changed, one supply bag is easily disconnected from the pump cassette and a second medicine in another supply bag is conveniently attached to the pump cassette.

Because the supply tube has been in fluid contact with a patient, the used cassette tubing and or reservoir bag may contain bodily fluids that passed up though the tubing. Thus, the tubing and or reservoir bag are considered medical waste and must be disposed of accordingly. Many principalities now have laws that forbid medical waste from being placed in landfills. The preferred disposal method is by incineration. For proper incineration, the entire cassette with both the used tubing and reservoir bag along with the cassette shell need to be incinerated at relatively high temperatures compared to regular incineration temperatures of other waste products. Similarly, the remote cassette along with used tubing need to be incinerated at high temperature. The higher temperatures are needed for the proper decomposition of certain chemotherapy drugs and for certain rigid plastics such as poly-carbonate. The entire cassette has been incinerated even though the cassette shell can be easily re-sterilized and capable of being used again because the cassette is made to permanently retain the tubing and reservoir bags and it is too difficult and expensive to break into the cassette, cut the tubing and rebuild the cassette with a new bag and tubing in place.

The pumps are constructed for long durability. A typical cassette containing a reservoir bag is capable of holding only one hundred milliliters (100 ml.). The pump thus can pump many cassettes each day as needed. The pump during its useful life can be used with many thousands of cassettes over several years.

The increasing expense and difficulties of proper disposal of the cassette assembly necessitates that only the waste be disposed of and other parts be repaired and reused when possible and convenient. The re-use of the cassette shell can save much plastic and reduce the amount of unnecessary incineration and the unwanted particulates and gasses produced by incineration.

What is needed is a cassette shell and pump plate that allow for easy removal of tubing and reservoir bags and easy reinstallation of replacement supply tubes and reservoir bags without the need for drilling, cutting or tearing of the cassette, bags, or tubing thus reducing the exposure of the fluids to the exterior. What is needed is a recyclable cassette that allows the bags and tubes to remain closed until proper incineration.

SUMMARY OF THE DISCLOSURE

In accordance with one aspect of the invention, a reusable cassette casing for a medical infusion pump system is removably attachable to a pump housing via a mounting system. The cassette casing includes a plate member that is adjacent a squeezable tube connected to a reservoir bag. The tube is squeezable by a peristaltic type pump in said pump housing pressing the tube flat against the plate member thus providing a pumping action on the fluid within the tube. The cassette casing includes the plate member being removably secured to an open end of a cassette shell member via a plurality of connection devices. The open end of the cassette shell is sized and shaped to provide removal of a reservoir bag from an interior of the shell and insertion and installation of a second reservoir bag within the interior of the shell. The connection devices cooperate with the shell and plate member to reconnect the plate member to the shell member once a new replacement bag and tube are installed.

Preferably the connection devices include a plurality of resilient prongs connected to a one of the plate member about its periphery and the shell about the open end. The connection devices also include a plurality of notches sized to receive said resilient prongs in the other of said plate member about its periphery and said shell about said top open end. The connection devices are constructed for automatically locking and affixing the plate member to the shell when the plate member is positioned to a closed position.

In one embodiment, the connection devices include a slide channel at the top open end of the shell. The plate member has a peripheral edge section slidably receivable in the slide channel of said shell to be slidable between an open position and a closed position. A latch device automatically locks the plate member in the closed position when the plate is slid to the closed position.

According to another aspect of the invention, a reusable pumping plate member for a medical infusion pump system includes the mounting system for mounting the plate member to a pump assembly. The mounting system includes a hook-like protrusion extending from the plate member and is sized to be engageable to a latch mechanism on said pump assembly. The hook-like protrusion has a distal end spaced from a main plate section of the plate member to provide for lateral engagement of the tube member under said hook like protrusion and lateral disengagement of said tube member out from under said hook like protrusion. The plate member includes a slot extending from a peripheral edge of the plate member and under the hook-like protrusion for allowing the tube member or reservoir bag to laterally be received in the slot and laterally disengaged from the slot when the plate member is disconnected from the cassette shell member.

Preferably, the plate member includes a tube positioning retainer hook having a distal end spaced from the main plate section of the plate member a distance less than the diameter of said tube member to allow the tube member to be laterally engaged and retained under said tube positioning hook. The tube member is squeezable to laterally engage and disengage from the tube positioning hook.

BRIEF DESCRIPTION OF THE DRAWINGS

Reference now is made to the accompanying drawings in which:

FIG. 1 is a perspective view of a cassette assembly according to the invention attachable to a pump (shown in phantom);

FIG. 2 is an exploded front perspective view of the cassette assembly shown in FIG. 1;

FIG. 3 is a cross sectional view taken along lines 1—1 shown in FIG. 1;

FIG. 4 is a side perspective and enlarge fragmentary view illustrating the slot and latch mechanism of the plate member;

FIG. 9 is a view similar to FIG. 2 illustrating a fourth embodiment;

FIG. 10 is fragmentary perspective and exploded view illustrating a fifth embodiment;

FIG. 11 is a perspective view illustrating a sixth embodiment;

FIG. 12 is a view similar to FIG. 2 illustrating a seventh embodiment;

FIG. 13 is an enlarge fragmentary side elevational view taken illustrating the tube retainer shown in FIG. 12;

FIG. 14 is a perspective view of a remote cassette in accordance with the invention; and FIG. 15 is a fragmentary view from a different perspective of the cassette shown in FIG. 14.

DETAILED DESCRIPTION OF THE PREFERRED EMBODIMENT

Figure 5:
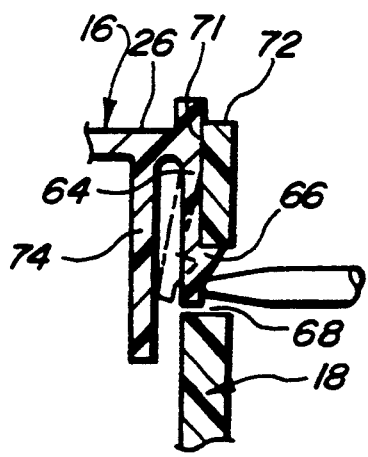
FIG. 5 is an enlarged fragmentary cross sectional view taken along line 5—5 shown in FIG. 1.

Referring now to FIGS. 1, 2, 3, and 4, an ambulatory medical infusion pump assembly 10 includes a pump housing 12 and a cassette assembly 14 removably attached to the housing 12. The cassette assembly 14 has a pump plate 16 attached to a cassette shell 18 that together forms a casing 20 which contains a flexible reservoir bag 22 at its interior chamber 27. The bag 22 has an upper bag section 23 that is fitted through a tube port 25. A pliable tube 24 is attached to the bag section 23 and is positioned against the exterior side 26 of the pump plate 16. Appropriate guides 28 and tube retainer 30 retain the tube 24 in its proper position against plate 16. The tube 24 is connected to a microbore tubing 32 that extends from the pump housing 12 and cassette casing 20. A Luer lock 34 is connected at the distal end 36 of the microbore tubing 32 to be connected to infusion tubing (not shown). A clamp 35 is installed about tubing 32 and has a tapered slot 37 which can be used to crimp the tubing 32 shut.

Referring now particularly to FIGS. 2 and 3, the tube retainer 30 has a base end 40 integrally affixed to the upper surface 26, an upper spanning section 42 and a distal retaining hook section 44 that forms a gap 46 with the upper surface 26. The gap 46 is smaller than the normal outer diameter of the pliable tube 24. However the tube 24 is pliable such that it can be deformed to be shorter than gap 46 and be laterally received through gap 46 to be positioned under retainer 30. Once under retainer 30, the tube assumed its normal outer diameter such that it is retained by the retainer and will not accidentally disengage from he retainer 30 through the narrow gap 46. However, the tube can be, when desired, disengaged from the retainer by a mere squeezing of the tube 24 and laterally moved out through gap 46.

Referring now to FIG. 2, the pump plate 16 has hooks 48 in proximity with retainer 30 to be removably attachable to appropriate mounts (not shown) in pump housing 12. The pump plate 16 also has a mounting latch hook 50, as shown in FIGS. 2 and 4, that has a base section 52 integrally formed with the pump plate upper surface 26, a spanning section 54, and a distal hook section 56. The hook section 56 forms a gap 58 between the itself and pump plate upper surface 26. The tube port 25 is an open slot through the pump plate 16 that extends from end section 62 at the periphery 64 of the pump plate 16. The tube 24 or reservoir bag upper section 23 can similarly be laterally engaged or disengaged into port 25 and under latch 50 by passing laterally through both the gap and through the port 25 when the pump plate is disengaged from the shell 18. When the pump plate 16 is installed on shell 18, the shell has end wall section 63 span gap 65 at end of port 25 between two arm sections 65 of pump plate 16.

The pump plate 16 has a plurality of resilient snap fit prongs 64 downwardly depending from its periphery 62 and outwardly extending tabs 66 at a distal end. The shell 18 has complementary notches 68 at its inner surface 69. The notches extend through to the exterior of the shell 18. Guide channels 71 may extend from the notches 68 to the upper edge 72.

A depending shielding flange 74 extends downwardly from the plate 16 and is slightly spaced inwardly from the prongs 64. The flange 74 provides two functions. Firstly, it acts as a limit stop to prevent over-flexing of the prongs 64 when a screwdriver or other prong type device is used to disengage the flange 66 from the notch 68 as illustrated in FIG. 5. Secondly, the shield prevents the prongs 64 from making undesirable contact with the bag 22 that is in the interior 27 of the casing 20.

When the bag 22 needs to replaced, the cassette assembly 14 is detached from the pump housing 12. If the reservoir bag 22 has any medicine in it, the bag 22 is completely emptied by using a medical syringe being used on luer lock 34. The tubing 24 is removed out from under the tube retainer 30 and out from between guides 28. The resilient prongs 64 are then flexed inwardly as shown in FIG. 5 to allow the plate 16 to be disassembled from the cassette shell 18. The tubing 24 is then laterally removed from port 25 through gap 65 such that the plate 16 is completely disengaged from the tubing and bag 22. The bag 22 can then be removed through the upper open end 76 of the shell 18.

The used bag 22 is then properly disposed as waste. The used bag 22 remains closed with luer lock 34 remaining on the tubing 32 until proper disposal. A new unused bag is then inserted into open end 76 into the interior 27 of shell 18 and the new replacement tubing 24 is laterally engaged into port 25 through gap 65 at the periphery of the pump plate 16. The plate 16 is then reconnected to the shell 18 by sliding the prongs 64 along channels 71 until the flanges 66 snap fit into notches 48. The new tubing 24 is then installed between channels 28 and squeezed under retainer 30.

At this point, the cassette assembly is packaged and sterilized under standard radiation or ethyleneoxide gas sterilization procedures. In this fashion, a medical cassette shell can be repaired and re-used with a new reservoir bag. Further use of the cassette shell 18 with third and subsequent bags can be accomplished by simply repeating the disassembly and reinstallation steps described above.

No milling or drilling of an access slot in shell 18 is necessary. No cutting of the tubes 24 or 32 are needed thereby reducing any exposure to the fluids within the tubing or bag 22. The new bag 22 may be preassembled with the luer lock 34 and clamp 35 before installation into the shell 18 thus simplifying the final assembly step. The used bag and tube may be removed and properly disposed of without disassembly of the lure lock 34 or clamp 35 from the tube 32.

In this fashion, the need for incinerating the entire shell after each use of a reservoir bag is eliminated and the shell may be used with a plurality of sequentially used reservoir bags.

Many embodiments of the shell and connecting devices between the shell and pump plate are compatible with the retainer 30, latch 50 and open port 25. Other examples of such compatible cassette casings are illustrated in FIGS. 6–11. For simplicity, parts that correspond with the parts of the above described first embodiment will have the same numbers.

Figure 6:
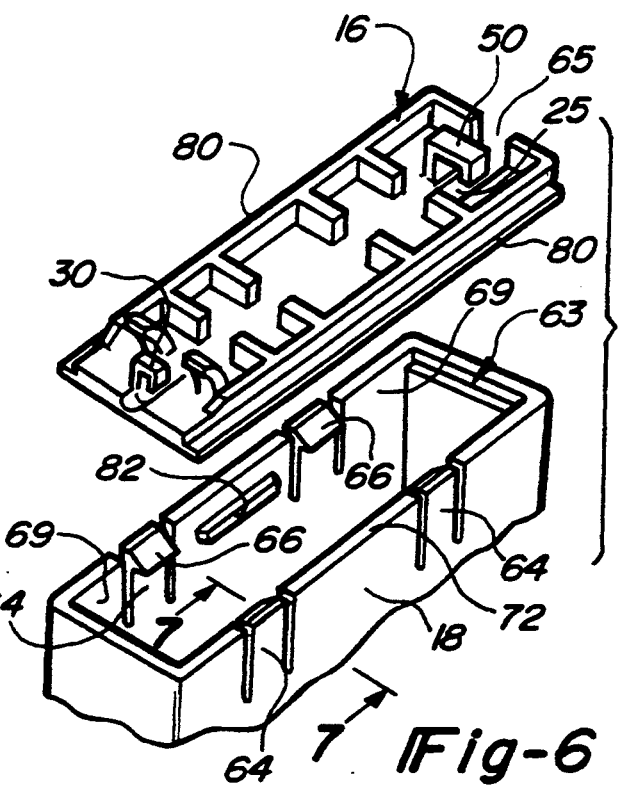
FIG. 6 is fragmentary view similar to FIG. 2 illustrating a second embodiment.
Figure 7:
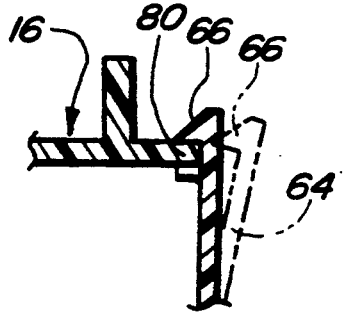
FIG. 7 is a view similar to FIG. 5 illustrating a connection device of the second embodiment.

As illustrated in FIGS. 6 and 7, the shell 18 has resilient prongs 64 extend to the top edge 72. Each prong 64 has an inwardly extending flange 66 that engages the peripheral edge 80 of pump plate 16. A ledge 82 on the interior wall 69 provides for a stop for the pump plate 16 when its mounted on shell 18. Removal of the pump plate 16 is achieved by outward flexing of the prongs 64 to disengage the flanges 66 from the peripheral edge 80 of the pump plate 16 and lifting of the pump plate 16 off shell 18.

Figure 8:
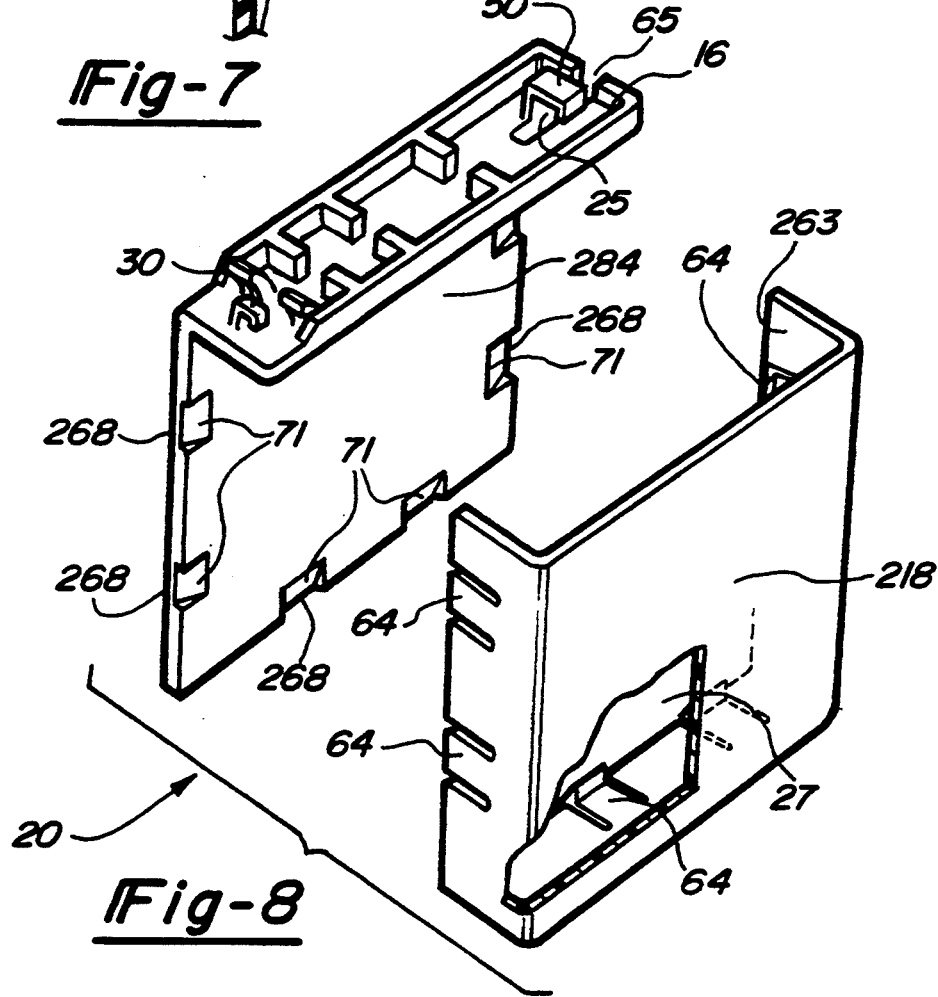
FIG. 8 is a view similar to FIG. 2 illustrating a third embodiment.

FIG. 8 illustrates a third embodiment where the pump plate 16 is integrally formed with one other wall 84 of the casing 20. Part 218 of casing 20 has resilient prongs 64 with engaging flanges 66 that engage edge section 268 adjacent guide channels 71. When installed, the part 218 has wall section 263 span gap 65 in pump plate 16.

Other connecting devices can be used that incorporate a slide channel between two parts. FIG. 9 discloses an embodiment that has pump plate 16 integrally formed with wall 84 and floor 88. Edges 384 of the wall 84 slide in channel 390 of part 318 until resilient prongs 64 have flanges 66 snap into notches 68 in respective edges 384.

FIG. 10 illustrates a pump plate 16 that slides on the top end 72 of shell 18 in channel 490. The resilient prongs 64 at the top edge 72 has its flanges 66 snap fit into notches 68 in the periphery 80 of pump plate 16 when the pump plate is slid to the closed position.

FIG. 11 illustrates a hinged casing 520 that has a hinge 590 that allows part 518 to open up against part 522 that is integrally formed with pump plate 16. The part 518 has a wall section 563 that opens up gap 65 of slot 25 when the casing 520 is opened.

Other constructions of a reusable casing for an ambulatory medical infusion pump are foreseen. FIGS. 12 and 13 illustrates two halves 621 and 622 of casing 620 each having a half 615 and 617 of a pump plate 616 integrally formed therewith. The two halves 621 and 622 are attached through a plurality of prongs 64 and notches 68. As clearly shown in FIG. 13, each pump plate half 615 and 617 has a retainer half 630 that has distal upper end 640. Ends 640 abut each other to form a channel 642 thereunder that retains tube 24. Similarly latch halves 650 have distal upper ends 652 that abut each other to retain tube 24 thereunder as it passes into port 25. The halves 620 and 622 are disengagable such that, the retainer 30 and latch 50 disengage from tube 24 to allow the tube and bag to be removed from the casing 20.

Referring now to FIGS. 14 and 15, the concept of the retainer 30 and latch 50 with open slot or port 25 can also be applied to a remote pumping plate casing 720 that has a pumping plate 16 and shell 718. A tube assembly 722 includes a pliable tube section 24 and microbore tubing 32 and luer lock 34. The other end 735 of the tubing 24 is connected to microbore tubing 737 that extends from the pump housing 12 and casing 720. Tube end 735 passes into port 25 and to a rubber gasket 741 installed in slot 743 in end 747 of shell 718 as shown clearly in FIG. 15. Slot 743 has detentes 749 that retain the gasket 741 in position. The microbore tubing 737 has a lock fastener 748 connected at distal end 751. The fasteners 34 and 748 are permanently secured to the tubing 32 and 737 respectively and the tubing 32 and 737 are permanently bonded to the soft tube section 24.

When the tubing assembly needs replacement, the casing 720 is detached in the conventional fashion from the pump housing 12. The tubing 722 is then disengages from retainer 30 and retainer 50 by merely sliding them out from thereunder and out of slot 25. The rubber gasket 741 can be disengaged from detentes 749 when sufficient manual force is applied.

The used tube assembly 722, after completely disengaged from the casing 720 is then properly disposed of as medical waste. The tube assembly 722 remains sealed with fasteners 34 and 748 remaining on the tube assembly 722 until proper disposal thereof. A new replacement tube assembly is then installed by sliding the tubing under retainer 30 and latch 50 and into slots 25 and 743. The tubing assembly 722 can be completely preassembled with the necessary microbore tubing and locks mounted at both distal ends, and with gasket 741 and clamp 35 mounted thereon.

At this point, the cassette assembly 720 is packaged and sterilized under either standard radiation procedures or ethyleneoxide gas sterilization procedures and is ready for sequential use. Further use of the cassette casing 720 with third and subsequent tubing assemblies can be accomplished by simply repeating the disassembly and reinstallation steps described above.

In this fashion, the need for incinerating the casing 720 after each tube assembly 72 is used is eliminated and the casing 720 may be used with a plurality of sequentially used tube assemblies 722.

Variations and modifications are possible without departing from the scope and spirit of the present invention as defined by the appended claims.

The embodiments in which an exclusive property or privilege is claimed are defined as follows:

1. A reusable cassette casing for a medical infusion pump system that is removably attachable to a pump housing via a mounting system, said cassette casing including a plate member that is adjacent a squeezable tube of a reservoir bag that is squeezable by a pump in said pump housing that presses said tube against said plate member, said cassette casing characterized by:
   said plate member being removably secured to a cassette shell via a plurality of connection devices:
   an open end of said cassette shell being sized and shaped to provide removal of a reservoir bag from an interior of said shell and insertion and installation of a second reservoir bag within said interior of said shell;
   said connection devices cooperating with said shell and plate member to removably mount said plate member to said shell at said open end of said shell and be usable to reconnect said plate member to said shell member; and
   said connection devices being moveable between a first and second position such that when in the second position, the plate member is free to be removable from said shell and when in a first position said connection device securely affix said plate member onto said shell.

2. A reusable cassette casing for a medical infusion pump system that is removably attachable to a pump housing via a mounting system, said cassette casing including a plate member that is adjacent a squeezable tube of a reservoir bag that is squeezable by a pump in said pump housing that presses said tube against said plate member, said cassette casing characterized by:
   said plate member being removably secured to a cassette shell via a plurality of connection devices:
   an open end of said cassette shell being sized and shaped to provide removal of a reservoir bag from an interior of said shell and insertion and installation of a second reservoir bag within said interior of said shell;
   said connection devices cooperating with said shell and plate member to removably mount said plate member to said shell at said open end of said shell and be usable to reconnect said plate member to said shell member;
   said connection devices including a plurality of resilient prongs connected to a one of said plate member about its periphery and said shell about said top open end; and
   said connection devices including a plurality of notches sized to receive said resilient prongs in the other of said plate member about its periphery and said shell about said top open end; and
   said connection devices constructed for automatically locking said plate in a closed position when positioned into said closed position over open end of said shell, said connection devices being constructed to be openable to allow said plate member to move to an open position with respect to said top open end of said shell.

3. A reusable cassette casing for a medic infusion pump system that is removably attachable to a pump housing via a mounting system, said cassette casing including a plate member that is adjacent a squeezable tube of a reservoir bag that is squeezable by a pump in said pump housing that presses said tube against said plate member, said cassette casing characterized by:
   said plate member being removably secured to a cassette shell via a plurality of connection devices:
   an open end of said cassette shell being sized and shaped to provide removal of a reservoir bag from an interior of said shell and insertion and installation of a second reservoir bag within said interior of said shell;
   said connection devices cooperating with said shell and plate member to removably mount said plate member to said shell at said open end of said shell and be usable to reconnect said plate member to said shell member;
   said connection devices including a slide channel at said top open end of said shell, said plate having a peripheral edge section slidably receivable in said slide channel of said shell to be slidable between an open position and a closed position; and
   a latch device for automatically locking said plate in said closed position when slid into said closed position, said latch device being openable to allow said plate member to slide to the open position.

4. A reusable cassette casing for a medical infusion pump system that is removably attachable to a pump housing via a mounting system, said cassette casing including a plate member that is adjacent a squeezable tube of a reservoir bag that is squeezable by a pump in said pump housing that presses said tube against said plate member, said cassette casing characterized by:
   said plate member being removably secured to a cassette shell via a plurality of connection devices:
   an open end of said cassette shell being sized and shaped to provide removal of a reservoir bag from an interior of said shell and insertion and installation of a second reservoir bag within said interior of said shell;
   said connection devices cooperating with said shell and plate member to removably mount said plate member to said shell at said open end of said shell and be usable to reconnect said plate member to said shell member; and
   said mounting system for mounting said plate member to a pump assembly including a hook-like protrusion that is sized to be engageable to a latch mechanism on said pump assembly;
   said hook-like protrusion having a distal end space from a main plate section of said plate member to provide for lateral engagement of a tube member under said hook like protrusion and lateral disengagement of said tube member out from under said hook like protrusion; and said plate member including a slot extending from a peripheral edge of said plate member and under said hook-like protrusion for allowing said tube member to laterally be received in said slot and laterally disengaged from said slot when said plate member is disconnected from said cassette shell member.

5. A cassette casing as defined in claim 4 further characterized by:
said plate member including a tube positioning hook having a distal end spaced from said main plate section of said plate member a distance less than the diameter of said tube to allow said tube to be laterally engaged and retained under said tube positioning hook; and
said tube being squeezable to laterally engage and disengage from said tube positioning hook.

6. A cassette casing as defined in claim 4 further characterized by:
said connection devices including a plurality of resilient prongs connected to a one of said plate member about its periphery and said shell about said top open end; and
said connection devices including a plurality of notches sized to receive said resilient prongs in the other of said plate member about its periphery and said shell about said top open end; and
said connection devices constructed for automatically locking said plate in a closed position when positioned into said closed position over open end of said shell, said connection devices being constructed to be openable to allow said plate member to move to an open position with respect to said top open end of said shell.

7. A reusable cassette casing for a medical infusion pump system that is removably attachable to a pump housing via a mounting system, said cassette casing including a plate section that is adjacent a squeezable tube of a reservoir bag that is squeezable by a pump in said pump housing against said plate section, said cassette casing characterized by:
said plate section Being integrally formed with a first shell section member;
said first cassette shell section member being removably connected to a second cassette shell section member via a connector mechanism to define an interior of said cassette casing and movable between an open position to open said casing to provide removal of said reservoir bag from said interior and insertion and installation of a second reservoir bag within said interior of said casing and closed position after said second bag is installed.

8. A cassette casing as defined in claim 7 further characterized by:
said mounting system for joining said plate member to a pump assembly including a hook-like protrusion that is sized to be engageable to a latch mechanism on said pump assembly;
said hook-like protrusion having a distal end space from a main plate section of said plate member to provide for lateral engagement of a tube member under said hook like protrusion and lateral disengagement of said tube member out from under said hook like protrusion; and
said plate member including a slot extending from a peripheral edge of said plate member and under said hook-like protrusion for allowing said tube member to laterally be received in said slot and laterally disengaged from said slot when said plate member is disconnected from said cassette shell member.

9. A cassette casing as defined in claim 8 further characterized by:
said plate member including a tube positioning hook having a distal end spaced from said main plate section of said plate member a distance less than the diameter of said tube to allow said tube to be laterally engaged and retained under said tube positioning hook; and
said tube being squeezable to laterally engage and disengage from said tube positioning hook.

10. A reusable pumping plate member for a medical infusion pump system that is removably attachable to a pump housing via a mounting system, said plate member is adjacent a squeezable tube member that transports fluid from a reservoir bag that is squeezable by a pump in said pump housing by pressing said tube against said plate member, said plate member characterized by:
said mounting system for joining said plate member to a pump assembly including a hook-like protrusion extending from said plate member and is sized to be engageable to a latch mechanism on said pump assembly;
said hook-like protrusion having a distal end space from a main plate section of said plate member to provide for lateral engagement of said tube member under said hook like protrusion and lateral disengagement of said tube member out from under said hook like protrusion; and
said plate member including a slot extending from a peripheral edge of said plate member and under said hook-like protrusion for allowing said tube member to laterally be received in said slot and laterally disengageable from said slot when said plate member is disconnected from said cassette shell member.

11. A plate member as defined in claim 10 further characterized by:
said plate member including a tube positioning hook having a distal end spaced from a main plate section of said plate member a distance less than the diameter of said tube member to allow said tube member to be laterally engaged and retained under said tube positioning hook; and
said tube member being squeezable to laterally engage and disengage from said tube positioning hook.

12. A reusable cassette casing for a medical infusion pump system that is removably attachable to a pump housing via a mounting system, said cassette casing including a plate member that is adjacent a squeezable tube of a reservoir bag that is squeezable by a pump in said pump housing that presses said tube against said plate member, said cassette casing characterized by:
said plate member being removably secured to a cassette shell via a connection device:
an open end of said cassette-shell being sized and shaped to provide removal of a reservoir bag from an interior of said shell and insertion and installation of a second reservoir bag within said interior of said shell;
said connection device cooperating with said shell and plate member to removably mount said plate member to said shell at said open end of said shell and be usable to reconnect said plate member to said shell member; and
said connection device being moveable between a first and second position such that when in the second position, the plate member is free to be removable from said shell and when in a first position securely affixes said plate member onto said shell.

* * * * *